United States Patent [19]

Broaddus

[11] Patent Number: 4,849,222

[45] Date of Patent: Jul. 18, 1989

[54] MIXTURES FOR TREATING HYPERCHOLESTEROLEMIA

[75] Inventor: Charles D. Broaddus, Cincinnati, Ohio

[73] Assignee: The Procter & Gamble Company, Cincinnati, Ohio

[21] Appl. No.: 29,825

[22] Filed: Mar. 24, 1987

[51] Int. Cl.$^4$ .................. A61K 35/78; A61K 31/70
[52] U.S. Cl. .................. 424/195.1; 514/23; 514/824
[58] Field of Search ............... 424/195.1; 514/23, 824

[56] References Cited

U.S. PATENT DOCUMENTS

| | | | |
|---|---|---|---|
| 2,831,854 | 4/1958 | Tucker et al. | 260/234 |
| 3,455,714 | 7/1969 | Bishop et al. | 106/205 |
| 3,579,548 | 5/1971 | Whyte | 260/410.7 |
| 3,600,186 | 8/1971 | Mattson et al. | 99/1 |
| 3,954,976 | 5/1976 | Mattson et al. | 514/23 |
| 3,963,699 | 6/1976 | Rizzi et al. | 260/234 |
| 4,005,195 | 1/1977 | Jandacek | 514/23 |
| 4,005,196 | 1/1977 | Jandacek et al. | 514/23 |
| 4,034,083 | 7/1977 | Mattson | 514/23 |
| 4,241,054 | 12/1980 | Volpenhein et al. | 514/23 |
| 4,264,583 | 4/1981 | Jandacek | 514/182 |
| 4,321,263 | 3/1982 | Powell et al. | 424/195.1 |
| 4,382,924 | 5/1983 | Berling et al. | |
| 4,386,213 | 1/1983 | Hollenbach et al. | 426/590 |
| 4,461,782 | 7/1984 | Robbins et al. | 426/549 |
| 4,517,360 | 5/1985 | Volpenhein | 536/119 |
| 4,518,772 | 5/1985 | Volpenhein | 536/119 |

OTHER PUBLICATIONS

J. E. Garvin, D. T. Forman, W. R. Fiseman, C. R. Phillips, Proc. Soc. Exp. Biol. Med., 120, 744 (1965).
Forman, et al., ibid 127, 1060–1063 (1968).
Goodman and Gilman, The Pharmacologic Basis of Therapeutics 5th Ed. 979 (1975).

Primary Examiner—John W. Rollins
Attorney, Agent, or Firm—Jerry J. Yetter; Richard C. Witte

[57] ABSTRACT

Psyllium gum and polyol polyesters are administered orally to reduce blood cholesterol levels.

5 Claims, No Drawings

MIXTURES FOR TREATING HYPERCHOLESTEROLEMIA

TECHNICAL FIELD

The present invention relates to methods and compositions for reducing blood cholesterol levels by oral administration of psyllium derivatives and polyol polyesters.

BACKGROUND OF THE INVENTION

High blood cholesterol (hypercholesterolemia) is recognized as being a risk factor in cardiovascular disease which comprises a major health care problem, today. Epidemiological studies have demonstrated that, with few exceptions, populations consuming large quantities of saturated fat and cholesterol have a relatively high concentration of serum cholesterol and a high mortality rate from coronary heart disease. While it is recognized that other factors can also contribute to the development of cardiovascular disease, there appears to be a causal relationship between the concentration of serum cholesterol, in which hypercholesterolemia results in the accumulation of undesirable amounts of cholesterol in various parts of the circulatory system (arteriosclerosis) or in soft tissues (xanthomatosis), and coronary disease and coronary mortality rates.

A variety of dietary and drug regimens have been suggested for alleviating or preventing hypercholesterolemia. However, many of these have undesirable side effects or give suboptimal results. Accordingly, the search for materials which reduce blood cholesterol has continued.

In the present invention, nonabsorbable, nondigestible polyesters are used in combination with psyllium derivatives as orally-administered cholesterollowering compositions. In one mode, the compositions herein are additionally fortified with fat-soluble vitamins.

BACKGROUND ART

J. E. Garvin, D. T. Forman, W. R. Eiseman, and C. R. Phillips, *Proc. Soc. Exp. Biol. Med.*, 120, 744 (1965) describe the administration of psyllium (as METAMUCIL brand laxative) to human volunteers, resulting in a reduction in blood cholesterol levels. Also, see Forman, et al, ibid 127, 1060–1063 (1968).

There are a considerable number of United States patents relating to the use of nonabsorbable, nondigestible polyol polyesters of the type employed herein as cholesterol lowering agents. See, especially, U.S. Pat. Nos. 3,600,186; 4,005,195; 4,005,196 (includes fat-soluble vitamins); 4,034,083 (with fat-soluble vitamins); in various food compositions, e.g., U.S. Pat. Nos. 4,368,213; 4,461,782; 3,579,548; and in pharmaceutical products, e.g., U.S. Pat. Nos. 3,954,976; 4,241,054; 4,264,583; and 4,382,924. Manufacturing processes for the polyol polyesters are described in U.S. Pat. Nos. 3,963,699; 4,517,360; and 4,518,772. All of these patents are incorporated herein by reference.

Psyllium derivatives (also referred to as "gums" or "hydrophilic mucilloids") of the type employed herein are known commercially as METAMUCIL brand laxative and are described in Goodman and Gilman, *The Pharmacologic Basis of Therapeutics* 5th Ed. 979 (1975). See also U.S. Patents 3,455,714 and 4,321,263.

SUMMARY OF THE INVENTION

The present invention encompasses orally-administered compositions of matter for reducing blood cholesterol levels in humans or lower animals, comprising a mixture of:
 (a) psyllium seed gum or source of psyllium seed gum; and
 (b) a nonabsorbable, nondigestible polyol polyester.

The invention also encompasses a method for reducing blood cholesterol in a patient (including both humans and lower animals) in need of such treatment, comprising orally administering to said patient a safe and effective amount of:
 (a) psyllium seed gum or a source of psyllium seed gum; and
 (b) a nonabsorbable, nondigestible polyol polyester; or
 (c) mixtures of (a) and (b).

The compositions herein can be provided in bulk form as granules, or in unit dosage forms such as tablets, capsules, effervescing granules or tablets, and the like. The compositions can contain various flavorings, extenders, tableting aids, and the like, well-known to formulators of pharmaceutical products.

In an optional embodiment, the compositions herein can be fortified with fat-soluble vitamins, since the polyol polyesters can undesirably deplete the body's stores of these vitamins.

All percentages, ratios and proportions herein are by weight, unless otherwise specified.

DETAILED DESCRIPTION OF THE INVENTION

The psyllium gum used in the practice of this invention comes from psyllium seed, from plants of the *Plantago* genus. Various species such as *Plantago lanceolate, P. rugelii,* and *P. major,* are known. Commercial psyllium includes the French (black; *Plantago indica*), Spanish (*P. psyllium*) and Indian (blond; *P. ovata*). The gum content of the psyllium varies: French psyllium, 11.8%, Indian psyllium, 30.9%; and German psyllium, 11.5%. Indian (blond) psylllium is preferred for use herein.

The psyllium gum (or "hydrophilic mucilloid") is located in the seed coat, from which it is readily extractable by water. Thus, intact or macerated seeds can be used in the practice of this invention; however, it is more typical to remove the seed coats from the rest of the seed by, for example, slight mechanical pressure, and then to use only the coats as a source of the gum. In the practice of the present invention it is convenient and typical to use macerated seed coats in the final formulation as the source of the psyllium seed gum, but, in an alternative procedure, the seed coats are extracted with water to remove the desired gum for use in the compositions and methods herein.

The nonabsorbable, nondigestible polyol polyesters (or, simply, polyesters) employed in this invention comprise certain polyols, especially sugars or sugar alcohols, esterified with at least four fatty acid groups. Accordingly, the polyol starting material must have at least four esterifiable hydroxyl groups. Examples of preferred polyols are sugars, including monosaccharides and disaccharides, and sugar alcohols. Examples of monosaccharides containing four hydroxyl groups are xylose and arabinose and the sugar alcohol derived from xylose, which has five hydroxyl groups, i.e., xylitol. (The monosaccharide, erythrose, is not suitable in the practice of this invention since it only contains three hydroxyl groups; but the sugar alcohol derived from erythrose, i.e., erythritol, contains four hydroxyl groups and accordingly can be used.) Suitable five hydroxyl group-containing monosaccharides are galactose, fructose, and sorbose. Sugar alcohols containing six -OH groups derived from the hydrolysis products of sucrose, as well as glucose and sorbose, e.g., sorbitol, are also suitable. Examples of disaccharide polyols which can be used include maltose, lactose, and sucrose, all of which contain eight hydroxyl groups.

Preferred polyols for preparing the polyesters for use in the present invention are selected from the group consisting of erythritol, xylitol, sorbitol, glucose and sucrose. Sucrose is especially preferred.

The polyol starting material having at least four hydroxyl groups must be esterified on at least four of the -OH groups with a fatty acid containing from about 8 to about 22 carbon atoms. Examples of such fatty acids include caprylic, capric, lauric, myristic, myristoleic, palmitic, palmitoleic, stearic, oleic, ricinoleic, linoleic, linolenic, eleostearic, arachidic, arachidonic, behenic, and erucic acid. The fatty acids can be derived from naturally occurring or synthetic fatty acids; they can be saturated or unsaturated, including positional and geometrical isomers, depending on the desired physical properties (e.g., liquid of a desired viscosity or solid) of the polyol fatty acid polyester compound being prepared.

Fatty acids per se or naturally occurring fats and oils can serve as the source for the fatty acid component in the polyol fatty acid polyester. For example, rapeseed oil provides a good source of $C_{22}$ fatty acids. The $C_{16}$-$C_{18}$ fatty acids can be obtained from tallow, soybean oil, and cottonseed oil. Shorter chain fatty acids can be obtained from coconut, palm kernel, and babassu oils. Corn oil, lard, oil, palm oil, peanut oil, safflower seed oil, sesame seed oil, and sunflower seed oil are examples of other natural oils which can serve as the course of the fatty acid used to prepare the polyesters herein.

Preferred fatty acids for preparing the polyol polyesters herein are the C14 to C18 acids, and are most preferably selected from the group consisting of myristic, palmitic, stearic, oleic, and linoleic fatty acids. Thus, natural fats and oils which have a high content of these fatty acids represent preferred sources for the fatty acid component, i.e., soybean oil, olive oil, cottonseed oil, corn oil, tallow and lard.

The polyol fatty acid polyesters useful in this invention must contain at least four fatty acid ester groups. Polyol fatty acid polyester compounds that contain three or less fatty acid ester groups are digested in and the products of digestion are absorbed from the intestinal tract much in the manner of ordinary triglyceride fats, whereas the polyol fatty acid polyester compounds that contain four or more fatty acid ester groups are substantially nondigestible and consequently nonabsorbable by the human body. It is not necessary that all of the hydroxyl groups of the polyol be esterified with fatty acid, but it is preferable that the polyester contain no more than two unesterified hydroxyl groups. Most preferably, substantially all of the hydroxyl groups of the polyol are esterified with fatty acid, i.e., the compound is substantially completely esterified. The fatty acids esterified to the polyol molecule can be the same or mixed.

To illustrate the above points, a sucrose fatty triester would not be suitable for use herein because it does not contain the required four fatty acid ester groups. A sucrose tetra-fatty acid ester would be suitable, but is not preferred because it has more than two unesterified hydroxyl groups. A sucrose hexa-fatty acid ester would be preferred because it has no more than two unesterified hydroxyl groups. Highly preferred compounds in which all the hydroxyl groups are esterified with fatty acid include the sucrose octa-fatty acid esters.

In any given polyol fatty acid polyester compound the fatty acid ester groups can be selected on the basis of the desired physical properties of the compound. For example, the polyol polyesters which contain unsaturated fatty acid ester groups and/or a preponderance of short chain, e.g., $C_{12}$, fatty acid ester groups are generally liquid at room temperature. The polyols esterified with longer chain and/or saturated fatty acid groups such as stearoyl are solids at room temperatures.

The following are nonlimiting examples of specific polyol fatty acid polyesters containing at least four fatty acid ester groups suitable for use in the present invention: glucose tetraoleate, glucose tetrastearate, the glucose tetraesters of soybean oil fatty acids, the mannose tetraesters of mixed tallow fatty acids, the galactose tetraesters of olive oil fatty acids, the arabinose tetraesters of cottonseed oil fatty acids, xylose tetralinoleate, galactose pentastearate, sorbitol tetraoleate, the sorbitol hexaesters of olive oil fatty acids, xylitol pentapalmitate, the xylitol tetraesters of substantially completely hydrogenated cottonseed oil fatty acids, sucrose tetrastearate, sucrose pentastearate, sucrose hexaoleate, sucrose octaoleate, the sucrose octaesters of partially or substantially completely hydrogenated soybean oil fatty acids and the sucrose octaesters of peanut oil fatty acids.

As noted above, highly preferred polyol fatty acid esters are those wherein the fatty acids contain from about 14 to about 18 carbon atoms and are thus derived from such natural materials as soybean oil and olive oil. Examples of such compounds are the erythritol tetraesters of olive oil fatty acids, erythritol tetraoleate, xylitol pentaoleate sorbitol hexaoleate, sucrose octaoleate, and the sucrose hexa-, hepta- and octaesters of soybean oil fatty acids, partially or substantially wholly hydrogenated.

The polyol fatty acid polyesters suitable for use herein can be prepared by a variety of methods well known to those skilled in the art. These methods include: transesterification of the polyol with methyl, ethyl or glycerol fatty acid esters using a variety of catalysts; acylation of the polyol with a fatty acid chloride; acylation of the polyol with a fatty acid anhydride; and acylation of the polyol with a fatty acid, per se. As an example, the preparation of polyol fatty acid esters is described in U.S. Pat. No. 2,831,854, incorporated herein by reference. The most highly preferred methods of preparing the polyol polyesters used herein are disclosed in U.S. Pat. Nos. 4,517,360 and 4,518,772, incorporated herein by reference.

Specific, but nonlimiting, examples of the preparation of polyol fatty acid esters suitable for use in the practice of this invention are as follows.

Erythritol tetraoleate—Erythritol and a five-fold molar excess of methyl oleate are heated at 180° C., under vacuum, with agitation, in the presence of sodium methoxide catalyst over two reaction periods of several hours each. The reaction product (predominately erythritol tetraoleate) is refined in petroleum ether and crystallized three times from several volumes of acetone at 1° C.

Xylitol pentaoleate—Xylitol and a five-fold molar excess of methyl oleate in dimethylacetamide (DMAC) solution are heated at 180° C. for five hours in the presence of sodium methoxide catalyst, under vacuum. During this time the DMAC is removed by distillation. The product (predominately xylitol pentaoleate) is refined in petroleum ether solution and, after being freed of petroleum ether, is separated as a liquid layer four times from acetone at ca. 1° C. and twice from alcohol at ca. 10° C.

Sorbitol hexaoleate is prepared by essentially the same procedure used to prepare xylitol pentaoleate except that sorbitol is substituted for xylitol.

Sucrose octaoleate is prepared by substantially the same procedure as that used to prepare erythritol tetraoleate except that sucrose is substituted for erythritol.

The fat-soluble vitamins can optionally be used to fortify the foregoing polyesters. It will be appreciated that commercial preparations of the appropriate vitamins and/or appropriate vitamin mixtures which provide vitamins A, D, E and K can be used herein. See U.S. Pat. No. 4,034,083 for details of the role of these vitamins in metabolism and their use in combination with polyesters of the type used in this invention.

In general terms, the vitamins are classified as either "fat-soluble" or "water-soluble". The fat-soluble vitamins are used to fortify the polyester materials herein. The fat-soluble vitamins include vitamin A, vitamin D, vitamin E, and vitamin K.

The amount of the individual fat-soluble vitamins used to fortify the present compositions can vary with the age of the recipient, the dosage regimen used, and the amount of the vitamin ingested from other dietary sources. For example, in younger, growing children or in pregnant females it is recognized that larger amounts of any given vitamin should be ingested to supply optimal nutritional benefits than are needed with adult males. If the user of the present compositions happens to ingest foods which are extremely rich in a given fat-soluble vitamin, less of that vitamin need be used in the present compositions to insure adequate intestinal uptake for good nutrition. In any event, an attending physician can, if so desired, measure the amount of fat-soluble vitamins in the plasma. Based on these data, the appropriate type and amount of fat-soluble vitamin used to fortify the polyesters herein can then be determined on an individual basis.

More simply, the formulator of the compositions herein can fortify the polyesters with a recommended daily allowance (RDA), or increment or multiple of an RDA, of any of the fat-soluble vitamins to insure that the user of the compositions will maintain a nutritionally adequate uptake of said vitamins. For example, with vitamin A a daily amount in the range of 20 international units (I.U. to about 57 I.U. per kilogram of body weight can be employed. With vitamin D, fortification of the compositions to provide about 400 I.U., total, per day is ample. When supplementing with vitamin E, the amount of the vitamin optimal for dietary intake ranges from 3-6 I.U. for infants to 25-30 I.U. total, per day, for adults. When supplementing with vitamin K, it is more difficult to estimate the amount to be ingested to provide adequate nutrition since the microorganisms living in the intestine can synthesize this vitamin. However, it is known that ingestion of from 0.5 mg.-1 mg. of vitamin K per day will prevent insufficiency.

METHOD OF TREATMENT

The treatment regimen herein comprises orally administering to a patient in need of having a lowered blood cholesterol level a safe and effective amount of the psyllium seed gum, or source thereof, and a nonabsorbable, nondigestible polyol polyester of the type described hereinabove, or, conveniently, mixtures of these two materials. Ingestion of from 1 g to 30 g of the psyllium material and from 5 g to 50 g of the polyester material is appropriate in most circumstances. However, this can vary with the size and condition of the patient, and the patient's blood cholesterol level. Such matters will, of course, be apparent to the attending physician. However, since the psyllium material and the polyol material are nontoxic and nonallergenic, even higher ingestion levels can be used without undue side effects, keeping in mind that the materials herein do have a laxative effect.

Treatment of the patient comprises chronic ingestion in order to lower and maintain the low cholesterol levels. Daily ingestion is preferred, and a daily ingestion of from about 5 g to about 15 g of the psyllium material and from about 15 g to about 50 g of the polyester material is most commonly used, with said ingestion being at two or three regularly spaced intervals throughout the day. Again, depending on the patient's size and cholesterol level in the patient's blood, this can be varied.

The preferred polyol polyesters used in the foregoing methods are: sucrose octaoleate, sucrose octalinoleate, sucrose oltapalmitate and mixtures thereof.

As mentioned, it is convenient to use the psyllium material and the polyester as a mixture. Thus, psyllium seed husks are prepared in a well-known manner and are admixed with the polyester, generally in a weight ratio of about 10:1 to about 1:10, preferably 3:1 to 1:3, conveniently 1:1. The materials readily admix, particularly when a liquid polyester such as sucrose octaoleate is used, and, at a weight ratio of 1:1 the resulting mixed composition has the appearance of resinous granules. These granules can be compacted to provide tablets or capsules, or, conveniently, can be spooned-out from the bulk mixture and either administered by the spoonful or admixed with water and drunk.

The following examples are typical of the compositions of this invention, but are not intended to be limiting thereof.

EXAMPLE I

| Ingredient | Amount (grams) |
| --- | --- |
| Blond psyllium husk (macerated) | 3.8 |
| Sucrose octaoleate | 10 |
| Flavor | As desired |

The psyllium husk and sucrose octaoleate are blended to form a unit dose composition. Three such unit doses are ingested each day, orally, during the course of two weeks to lower blood cholesterol. Thereafter, one dose per day is used, on a continuing basis.

EXAMPLE II

| Ingredient | Amount (grams) |
| --- | --- |
| Psyllium* | 7 |

-continued

| Ingredient | Amount (grams) |
|---|---|
| Sucrose octapalmitate** | 20 |

*As METAMUCIL brand laxative
**Vitaminized with Vitamin E

The psyllium and sucrose octapalmitate are each taken concurrently, by oral administration, three times per day, to reduce blood cholesterol levels.

It is to be appreciated that the laxative effect of psyllium is enhanced by the polyester materials herein.

EXAMPLE III

| Ingredient | Amount (grams) |
|---|---|
| Psyllium* | 7 |
| Sucrose polyester mixture** | 50 |

*As macerated husks 50:50 with dextrose
**Sucrose octaoleate/sucrose octalinoleate mixture The composition of Example III are administered in a single daily dose to reduce blood cholesterol.

While not intending to be limited by theory, it is surmised that the enhanced cholesterol lowering properties of the instant compositions are due to the differing modes of action of the two ingredients, the psyllium removing bile acids via the feces and the polyesters dissolving and removing cholesterol.

What is claimed is:

1. A composition of matter for reducing blood cholesterol levels, comprising:
   (a) psyllium seed gum or source of psyllium seed gum; and
   (b) a nonabsorbable, nondigestible polyol polyester at a weight ratio of component (a): component (b) from 3:1 to 1:3.

2. A method for reducing blood cholesterol in a patient in need of such treatment, by administering to said patient:
   (a) psyllium seed gum or a source of psyllium seed gum; and
   (b) a nonabsorbable, nondigestible polyol polyester; or
   (c) mixtures of (a) and (b); said method comprising oral ingestion of from 1 g to 30 g of component (a) and from 5 g to 50 g of component (b).

3. A method according to claim 2 which comprises chronic ingestion.

4. A method according to claim 3 which comprises daily ingestion.

5. A method according to claim 4 which comprises daily ingestion of from about 5 g to about 15 g of component (a) and from about 15 g to about 50 g of component (b), said ingestion being at two or three regularly-spaced intervals throughout the day.

* * * * *